United States Patent
Midha et al.

(10) Patent No.: US 10,206,865 B2
(45) Date of Patent: *Feb. 19, 2019

(54) ORAL COMPOSITIONS CONTAINING POLYMETHYLSILSESQUIOXANE PARTICLES

(71) Applicant: The Procter & Gamble Company, Cincinnati, OH (US)

(72) Inventors: Sanjeev Midha, Mason, OH (US); Michael Jude LeBlanc, Cincinnati, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/486,326

(22) Filed: Apr. 13, 2017

(65) Prior Publication Data
US 2017/0216192 A1 Aug. 3, 2017

Related U.S. Application Data

(63) Continuation of application No. 14/751,167, filed on Jun. 26, 2015, now Pat. No. 9,649,273, which is a
(Continued)

(51) Int. Cl.
*A61K 8/891* (2006.01)
*A61K 8/22* (2006.01)
(Continued)

(52) U.S. Cl.
CPC ............... *A61K 8/891* (2013.01); *A61F 2/07* (2013.01); *A61F 2/82* (2013.01); *A61F 2/86* (2013.01);
(Continued)

(58) Field of Classification Search
CPC . A61K 8/89; A61K 8/891; A61K 8/02; A61K 8/04; A61K 8/21; A61K 8/24;
(Continued)

(56) References Cited

U.S. PATENT DOCUMENTS 5,330,747 A 7/1994 Krzysik
5,513,987 A 5/1996 Hosoi et al.
(Continued)

FOREIGN PATENT DOCUMENTS

EP 535943 A1 4/1993
KR 2008/0039088 5/2008
(Continued)

OTHER PUBLICATIONS

"Tospearl® Silicone Microspheres: Design and Potential Applications", ip.com No. IPCOM000161959D; Dec. 12, 2007.
(Continued)

*Primary Examiner* — Carlos A Azpuru
(74) *Attorney, Agent, or Firm* — James E. Oehlenschlager

(57) ABSTRACT

Oral compositions containing a polyorganosilsesquioxane particle, preferably polymethylsilsesquioxane particles, an oxidizing agent and an orally-acceptable carrier. Method of using such compositions for the cleaning and polishing of dental enamel, such methods including the step of applying such oral care compositions to the teeth of a user.

20 Claims, 2 Drawing Sheets

R = Me, OH, H.

Related U.S. Application Data continuation of application No. 14/249,617, filed on Apr. 10, 2014, now Pat. No. 9,114,095.

(60) Provisional application No. 61/810,400, filed on Apr. 10, 2013.

(51) Int. Cl.

| | | |
|---|---|---|
| *A61Q 11/00* | (2006.01) | |
| *A61K 8/19* | (2006.01) | |
| *A61K 8/21* | (2006.01) | |
| *A61L 31/02* | (2006.01) | |
| *A61F 2/82* | (2013.01) | |
| *A61F 2/86* | (2013.01) | |
| *A61F 2/07* | (2013.01) | |
| *A61L 31/14* | (2006.01) | |
| *A61K 8/02* | (2006.01) | |

(52) U.S. Cl.
CPC ............ *A61K 8/025* (2013.01); *A61K 8/0241* (2013.01); *A61K 8/19* (2013.01); *A61K 8/21* (2013.01); *A61K 8/22* (2013.01); *A61L 31/022* (2013.01); *A61L 31/148* (2013.01); *A61Q 11/00* (2013.01); *A61F 2250/003* (2013.01); *A61K 2800/28* (2013.01); *A61K 2800/412* (2013.01); *A61K 2800/654* (2013.01)

(58) Field of Classification Search
CPC . A61K 8/27; A61K 8/34; A61K 8/342; A61K 8/43; A61K 8/55; A61K 8/58; A61K 8/942; A61Q 11/00
See application file for complete search history.

(56) References Cited

U.S. PATENT DOCUMENTS

| | | | |
|---|---|---|---|
| 5,603,920 | A | 2/1997 | Rice |
| 5,716,601 | A | 2/1998 | Rice |
| 5,952,400 | A | 9/1999 | Hosoi et al. |
| 6,569,408 | B1 | 5/2003 | Yue et al. |
| 6,589,512 | B1 | 7/2003 | Yue et al. |
| 6,649,147 | B1 | 11/2003 | Ye et al. |
| 6,682,722 | B2 | 1/2004 | Majeti et al. |
| 6,740,311 | B2 | 5/2004 | White et al. |
| 8,211,411 | B2 | 7/2012 | Deckner |
| 9,011,825 | B2 | 4/2015 | Midha et al. |
| 9,017,647 | B2 * | 4/2015 | Midha ................ A61K 8/89 424/49 |
| 9,114,095 | B2 | 8/2015 | Midha et al. |
| 9,186,306 | B2 | 11/2015 | Midha et al. |
| 9,192,563 | B2 * | 11/2015 | Midha ................ A61K 8/891 |
| 9,549,887 | B2 * | 1/2017 | Midha ................ A61Q 11/00 |
| 2003/0190336 | A1 | 10/2003 | Adams et al. |
| 2004/0186030 | A1 | 9/2004 | Hofrichiter et al. |
| 2005/0143268 | A1 | 6/2005 | Midha et al. |
| 2006/0111465 | A1 | 5/2006 | Jia et al. |
| 2008/0159967 | A1 | 7/2008 | Fultz et al. |
| 2008/0171001 | A1 | 7/2008 | Engelman et al. |
| 2009/0317339 | A1 | 12/2009 | Sharma et al. |
| 2010/0003201 | A1 | 1/2010 | Wahl |
| 2011/0020413 | A1 | 1/2011 | Gormley et al. |
| 2011/0056943 | A1 | 3/2011 | Ueda et al. |
| 2011/0135749 | A1 | 6/2011 | Sellinger et al. |
| 2012/0129135 | A1 | 5/2012 | Yang et al. |
| 2015/0290115 | A1 | 10/2015 | Midha et al. |

FOREIGN PATENT DOCUMENTS

| | | |
|---|---|---|
| WO | WO 1992/02454 | 2/1992 |
| WO | WO 2011/130009 | 10/2011 |
| WO | WO 2012/102750 | 8/2012 |

OTHER PUBLICATIONS

Momentive Tospearl 145 A Methylsilsesquioxane, material Safety Data Sheet, Version: 2.2, Dec. 16, 2011.
Momentive—Technical Data Sheet, Tospearl 3120, Mar. 20, 2013.
Marketing Bulletin—150KA —Momentive Mar. 20, 2013.
Marketing Bulletin Microspheres Jul. 2011.
Perry, Robert J., Applications for Crosslinked Siloxane Particles, ChemTech, Feb. 1999, vol. 29, No. 2.
PCT Search Report and Written Opinion for dated Sep. 10, 2014.
All Office Actions from U.S. Appl. No. 14/249,617, filed Apr. 10, 2014.
All Office Actions from U.S. Appl. No. 14/751,167, filed Jun. 26, 2015.

* cited by examiner

R = Me, OH, H.

ORAL COMPOSITIONS CONTAINING POLYMETHYLSILSESQUIOXANE PARTICLES

FIELD OF THE INVENTION

The present invention relates to oral care compositions containing abrasives, and methods for cleaning and polishing teeth using these compositions.

BACKGROUND OF THE INVENTION

An effective oral composition can maintain and preserve tooth appearance by removing dental stains and polishing the teeth. It may clean and remove external debris as well, which can aid the prevention of tooth decay and promote gingival health.

Abrasives in oral compositions aid in the removal of the tightly adherent pellicle film to which dental stains affix. Pellicle film usually comprises a thin acellular, glycoprotein-mucoprotein coating, which adheres to the enamel within minutes after teeth are cleaned. The presence of various food pigments lodged within the film accounts for most instances of teeth discoloration. An effective abrasive may remove the pellicle film with minimal abrasive damage to oral tissue, such as the dentin and enamel.

In addition to cleaning, it may be desirable for abrasive systems to provide polishing of tooth surfaces, as polished surfaces may be more resistant to ectopic deposition of undesirable components. Tooth appearance may be improved by imparting a polished character to the teeth, because the surface roughness, that is, its polish, affects light reflectance and scattering, which integrally relate to the teeth's visual appearance. The surface roughness also affects tooth feel. For example, polished teeth have a clean, smooth, and slick feel.

Numerous dentifrice compositions use precipitated silicas (among other materials) as abrasives. Precipitated silicas are noted and described in U.S. Pat. No. 4,340,583, Jul. 20, 1982, to Wason, EP Patent 535,943A1, Apr. 7, 1993, to McKeown et al., PCT Application WO 92/02454, Feb. 20, 1992 to McKeown et al., U.S. Pat. No. 5,603,920, Feb. 18, 1997, and U.S. Pat. No. 5,716,601, Feb. 10, 1998, both to Rice, and U.S. Pat. No. 6,740,311, May 25, 2004 to White et al.

While generally providing safe and effective cleaning of teeth, precipitated silicas in oral compositions may present compatibility problems and undesirable interactions with other desirable formula actives, such as metal ions, peroxide, fluoride and cationic antibacterials. These undesirable interactions may lead to reduction in the amount of active available in the formulation and/or reduction in product efficacy. These compatibility problems have been shown to be directly related to surface properties of precipitated silicas such as surface area, number of hydroxyl groups, and porosity. Another potential problem linked with surface properties of precipitated silicas used in oral composition is interactions with flavor components in the formula. This interaction may lead to production of off-flavors over the shelf life of the product, rendering the product unacceptable to consumers.

A need therefore exists for an abrasive system that first and foremost provides effective and safe cleaning and polishing of teeth and further has good compatibility with oral care actives such as key dentifrice components in oral compositions, particularly oral care compositions. In addition, there exists a continuing need for abrasives that can produce superior cleaning and polishing at reduced costs.

Commercially available polyorganosilsequioxane particles, more specifically polymethylsilsesquioxane silicone resin particles are commonly used in cosmetic applications to provide water repellency, lubricity, and impart a smooth, silky feel and/or appearance to skin. Materials sold by Momentive, under the tradename "TOSPEARL" are examples of such silicone resins, also known as T-resins or methylsilsesquioxanes. TOSPEARL 120A, 130A, 145A, 150KA and 2000B resins are commercially available spherical silicone resins available in 2.0, 3.0, 4.5, 5.0 and 6.0 micron median particle sizes, respectively.

SUMMARY OF THE INVENTION

The present invention relates to oral care compositions comprising a polyorganosilsesquioxane particle abrasive, preferably a polymethylsilsesquioxane particle abrasive. The present invention further relates to methods for cleaning and polishing dental enamel using these compositions.

It has surprisingly been found that polyorganosilsesquioxane particles, preferably polymethylsilsesquioxane particles, commonly used in cosmetic products to provide water repellency, lubricity, and imparting smooth, silky feel and/or appearance to skin, can provide abrasive cleaning properties to teeth when used in oral compositions. Further, such particles surprisingly and importantly offer improved stability with certain oral care actives over that observed with other commonly utilized oral care abrasives such as precipitated silica.

The present invention therefore utilizes polyorganosilsesquioxane particles in oral compositions, particularly in dentifrice compositions. Current dentifrice compositions available to consumers often use silica as a thickening agent as well as an abrasive, the silica typically used is precipitated silica. Without being bound by theory, it is believed that the polyorganosilsesquioxane particles, particularly polymethyl-silsesquioxane particles, have an inert surface and are less reactive than precipitated silica. Consequently, the polyorganosilsesquioxane particles may adsorb less of other components, such as flavors, actives, or cations, leading to better availability for these other components. For example, dentifrices incorporating polyorganosilsesquioxane particles have demonstrated superior stability in compositions with stannous ions and hydrogen peroxide. Without being bound by theory, it is also expected that polyorganosilsesquioxane particles would also demonstrate improved stability with fluoride, zinc, other cationic antibacterials, and similar materials that typically react negatively to precipitated silica.

The polyorganosilsesquioxane particles, preferably polymethylsilsesquioxane particles, of the present invention may provide one or more of these advantages. The present invention therefore relates to oral compositions and methods of using such oral compositions that may provide better active stability. The present invention's compositions and methods may provide better flavor aesthetics. And the present invention's compositions and methods may provide improved tooth cleaning without increased abrasiveness.

The present invention therefore relates to oral compositions containing at least 0.01%, by weight of the composition, of one or more polyorganosilsesquioxane particles; and an orally acceptable carrier; wherein the polyorganosilsesquioxane particles are substantially insoluble in the composition.

The present invention further relates to the above compositions wherein the polyorganosilsesquioxane particles are selected from polymethylsilsesquioxane particles, preferably having an average volume weighted mean particle size of from about 1 to about 20 microns. The present invention further relates to such compositions wherein the composition is substantially free of volatile carriers capable of solubilizing the organosiloxane particles in the composition and/or the composition is substantially free of polysiloxanes and/or the composition is substantially free of carbomer.

The present invention further relates to the above compositions wherein the composition comprises at least 0.01%, by weight of the composition, of an oral care active which may be selected from antibacterial agents, antiplaque agents, anticaries agents, antisensitivity agents, antierosion agents, oxidizing agents, anti-inflammatory agents, anticalculus agents, chelating agents, tooth substantive agents, antioxidants, analgesic agents, anesthetic agents, H-1 and H-2 antagonists, antiviral actives, nutrients and mixtures thereof or may be selected from stannous fluoride, sodium fluoride, monofluorophosphate, essential oils, mono alkyl phosphates, hydrogen peroxide, cetylpyridinium chloride, chlorhexidine, triclosan, and combinations thereof.

The present invention further relates to the above compositions wherein the polymethylsilsesquioxane particles are spherical smooth surface particles. The present invention further relates to the above compositions wherein the abrasive comprises from about 50% to about 100%, by weight of all the abrasive in the composition, of the polyorganosilsesquioxane particles.

The present invention further relates methods of reducing plaque, gingivitis, sensitivity, oral malodor, erosion, cavities, calculus, inflammation, and staining by administering to a subject's oral cavity one or more of the above compositions.

DETAILED DESCRIPTION OF THE INVENTION

Figure 1:
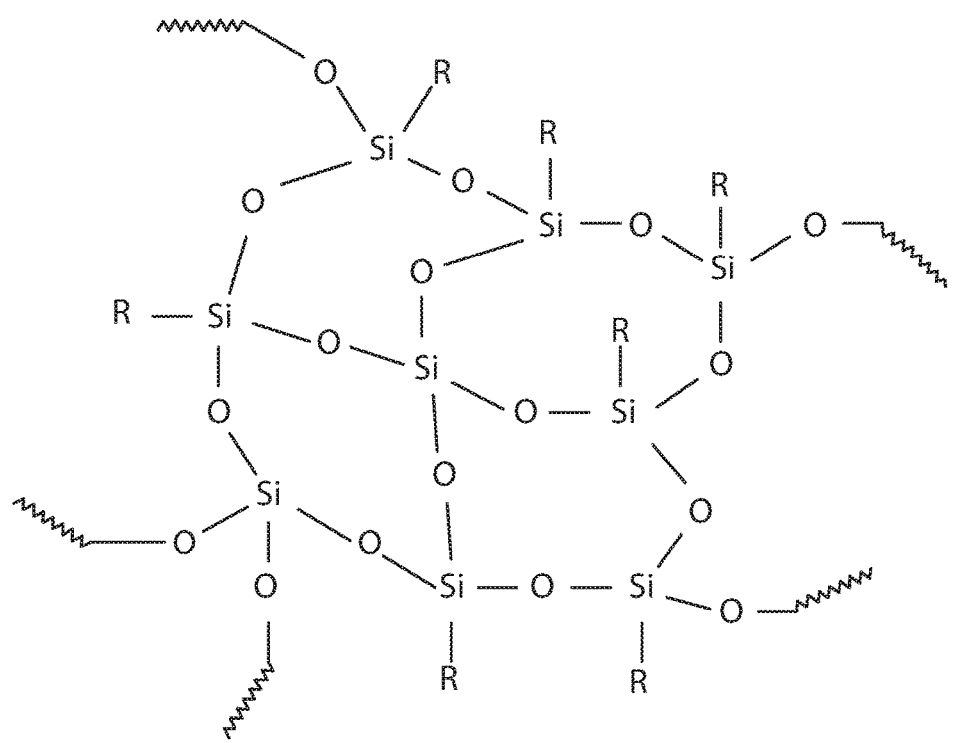
FIG. 1 is the general structure for polyorganosilsesquioxanes.

While the specification concludes with claims that particularly point out and distinctly claim the invention, it is believed the present invention will be better understood from the following description.

Definitions

The term "orally acceptable carrier" as used herein means a suitable vehicle or ingredient, which can be used to form and/or apply the present compositions to the oral cavity in a safe and effective manner.

The term "comprising" as used herein means that steps and ingredients other than those specifically mentioned can be added. This term encompasses the terms "consisting of" and "consisting essentially of." The compositions of the present invention can comprise, consist of, and consist essentially of the essential elements and limitations of the invention described herein, as well as any of the additional or optional ingredients, components, steps, or limitations described herein.

The term "effective amount" as used herein means an amount of a compound or composition sufficient to induce a positive benefit, an oral health benefit, and/or an amount low enough to avoid serious side effects, i.e., to provide a reasonable benefit to risk ratio, within the sound judgment of a skilled artisan. In one embodiment, "effective amount" means at least 0.01% of the material, by weight of the composition, alternatively at least 0.1%.

The term "oral composition" as used herein means a product that in the ordinary course of usage is retained in the oral cavity for a time sufficient to contact some or all of the dental surfaces and/or oral tissues for purposes of oral activity. In one embodiment, the composition is an "oral care composition" meaning that the composition provides a benefit when used in the oral cavity. The oral composition of the present invention may be in various forms including toothpaste, dentifrice, tooth gel, tooth powders, tablets, rinse, subgingival gel, foam, mouse, chewing gum, lipstick, sponge, floss, prophy paste, petrolatum gel, or denture product. In one embodiment, the oral composition is in the form of a paste or gel. In another embodiment, the oral composition is in the form of a dentifrice. The oral composition may also be incorporated onto strips or films for direct application or attachment to oral surfaces, or incorporated into floss.

The term "dentifrice" as used herein means paste, gel, powder, tablets, or liquid formulations, unless otherwise specified, that are used to clean the surfaces of the oral cavity. The term "teeth" as used herein refers to natural teeth as well as artificial teeth or dental prosthesis.

The term "polymer" as used herein shall include materials whether made by polymerization of one type of monomer or made by two (i.e., copolymers) or more types of monomers. The term "water soluble" as used herein means that the material is soluble in water in the present composition. In general, the material should be soluble at 25° C. at a concentration of 0.1% by weight of the water solvent, preferably at 1%, more preferably at 5%, more preferably at 15%.

The term "phase" as used herein means a mechanically separate, homogeneous part of a heterogeneous system.

The term "majority" as used herein means the greater number or part, a number more than half the total. The term "median" as used herein means the middle value in a distribution, above and below which lie an equal number of values.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt. %" herein. All molecular weights as used herein are weight average molecular weights expressed as grams/mole, unless otherwise specified.

Polyorganosilsesquioxane Particles

The oral compositions herein contain an effective amount of a polyorganosilsesquioxane particle, preferably a polymethylsilsesquioxane particle, to provide an abrasive, toothcleaning benefit. The oral compositions herein may include from about 0.1 to about 30%, by weight of the composition, of the particles. In another embodiment, the composition comprises from about 0.5 to about 20%, by weight of the composition, alternatively from about 1 to about 10%, by weight of the composition, of the particles. The composition may include from about 0.1% to about 50%, alternatively from about 1% to about 40%, alternatively from about 2% to about 35%, alternatively from about 4% to about 30%, alternatively from about 5% to about 25%, by weight of the composition, of the polyorganosilsequioxane, preferably polymethylsilsesquioxane, particles.

Polyorganosilsesquioxane particles are a type of silicone material formed by branched, cage-like oligosiloxanes with the general formula of $R_nSiX_mO_y$, where R is a non reactive substituent, usually Me or Ph, and X is a functional group H, OH, Cl or OR. These groups may be further condensed, to give highly crosslinked, insoluble polysiloxane networks. FIG. 1 provides the general structure. When R is methyl, the four possible functional siloxane monomeric units are described as follows: "M" is $Me_3SiO$, "D" is $Me_2SiO_2$, "T" is $MeSiO_3$ and "Q" is $SiO_4$. A network of only T-groups becomes polymethylsilsesquioxane. These materials are generally insoluble in typical oral care compositions, such as dentifrice.

Commercially available polymethylsilsesquioxane particles are commonly used in cosmetic applications to provide water repellency, lubricity, and impart a smooth, silky feel and/or appearance to skin. Materials sold by Momentive, under the tradename "TOSPEARL" are examples of such polymethylsilsesquioxane silicone resins, also known as T-resins or methylsilsesquioxanes. TOSPEARL 120A, 130A, CF600, 145A, 150KA and 2000B resins are commercially available spherical silicone resins available in 2.0, 3.0, 4.5, 4.5, 5.0 and 6.0 micron average median particle sizes, respectively. TOSPEARL 3120 is available with a 13.0 micron average median particle size. TOSPEARL 145A microspheres have a narrower particle size distribution and are particularly preferred for use herein. TOSPEARL 2000B have particles (on average) almost as small as TOSPEARL 145A microspheres and a slightly broader particle size distribution. TOSPEARL 3000A microspheres have an average particle size almost as large as TOSPEARL 2000B and has a slightly broader particle size distribution. TOSPEARL 145A, 2000B and 3000A all represent polymethylsilsesquioxane particles useful herein. Table 1 shows the published properties of TOSPEARL materials commercially available from Momentive.

The size distribution of particles in a given composition is plotted as cumulative volume percent as a function of particle size. Cumulative volume percent is the percent, by volume, of a distribution having a particle size of less than or equal to a given value and where particle size is the diameter of an equivalent spherical particle. The mean particle size in a distribution is the size in microns of the silica particles at the 50% point for that distribution. The size distribution and volume mean diameter for a particle size distribution may be calculated using a laser light scattering PSD system such as those commercially available from Malvern and/or determined using the methods disclosed in U.S. patent application 2007/0001037A1, published Jan. 4, 2007.

In plotting particle size, D [4,3] is the volume mean diameter, d(0.1) or D10 is the size (microns) of the particles sample below which 10% of the sample lies. d(0.5) or D50 is the size (microns) at which 50% of the particles sample is smaller and 50% is larger, also referred to as the "mass median diameter" or "MMD." d(0.9) or D90 is the size (microns) of the particles sample below which 90% of the sample lies. The width of the particle size distribution of a given composition can be characterized using a span ratio. As used herein, the span ratio is defined as the cumulative diameter of the particles in the tenth volume percentile minus the cumulative volume at the ninetieth percentile divided by the diameter of the particles in the fiftieth volume percentile, i.e. (D10–D90)/D50.

The average volume weighted mean particle size of the polyorganosilsesquioxane particles, preferably polymethylsilsesquioxane particles, may range from about 1 to about 20 microns, alternatively from about 1 to about 15 microns, alternatively from about 2 to about 15 microns, alternatively from about 2 to about 12 microns, alternatively from about 3 to about 12 microns, alternatively from about 2 to about 10 microns, alternatively from about 3 to about 7 microns, alternatively from about 3 to about 6 microns, alternatively from about 4 to about 6 microns. In an embodiment, the average volume weighted mean particle size of the polyorganosilsesquioxane, preferably polymethylsilsesquioxane particles, is from about 3 to about 8, alternatively from about 4 to about 7 microns and the d (0.1) is from about 2 to about 4, alternatively from about 2 to about 3 and the d (0.9) is from about 4 to about 9, alternatively from about 5 to about 8 microns.

The Specific Surface Area may be from about 15 to about 40, alternatively from about 15 to about 35, alternatively

TABLE 1

TOSPEARL 145A*
(Avg. particle size 4.5 microns)
TOSPEARL 3120*
(Avg. particle size 4.5 microns)
TOSPEARL CF 600*
(Avg. particle size 4.5 microns)
TOSPEARL 150*
(Avg. particle size 4.5 microns)

Typical Physical Properties

| Product Property | TOSPEARL 120A | TOSPEARL 145A | TOSPEARL 2000b | TOSPEARL 3000A | TOSPEARL 1110A |
|---|---|---|---|---|---|
| Average particle size; microns | 2 | 4.5 | 4-6 | 4-7 | 11 |
| pH | 7 | 7 | 7 | 7 | 7 |
| Specific Gravity (25. deg. C.) | 1.3 | 1.3 | 1.3 | 1.3 | 1.3 |
| Specific Surface Area, m2/g | 30 | 20 | 20-30 | 20-30 | 18 |
| Linseed Oil Absorption Rate (ml/100 g) | 75 | 60 | 60 | 60 | 56 | from about 10 to about 30, alternatively from about 15 m2/g to about 25 m2/g. The linseed oil absorption rate may be from about 50 to about 80, alternatively from about 55 to about 80, alternatively from about 55 to about 65 ml/100 g.

Polyorganosilsesquioxane particles formulated in a dentifrice composition may result in at least about 50%, 60%, 70%, 80%, or 90% compatibility with cations or other components. In some embodiments, the cation may be stannous.

PCR/RDA ratios. The Pellicle Cleaning Ratio (PCR) of the polyorganosilsesquioxane particles of the present invention, which is a measure of the cleaning characteristics of a dentifrice, ranges from about 40 to about 200 and preferably from about 60 to about 200. The compositions of the present invention may exhibit a PCR of at least 70, alternatively greater than about 80, alternatively greater than about 90.

The Radioactive Dentine Abrasion (RDA) of the inventive silica, which is a measure of the abrasiveness of the polyorganosilsesquioxane particles when incorporated into a dentifrice, is less than about 250, and may range from about 40 to about 230. The compositions of the present invention may exhibit an RDA score of less than 200, alternatively at most 100, alternatively at most 80.

The PCR values are determined by the method discussed in "In Vitro Removal of Stain with Dentifrice," G. K. Stookey, et al., *J. Dental Res.*, 61, 1236-9, 1982. The RDA values are determined according to the method set forth by Hefferren, *Journal of Dental Research*, July-August 1976, pp. 563-573; and described in Wason, U.S. Pat. Nos. 4,340, 583, 4,420,312, and 4,421,527. RDA values may also be determined by the ADA recommended procedure for determination of dentifrice abrasivity.

The PCR/RDA ratio of the polyorganosilsesquioxane particles, when incorporated into a dentifrice, may be greater than 1, indicating that the dentifrice is providing effective pellicle cleaning without too much abrasivity. The PCR/RDA ratio may also be at least about 0.5. The PCR/RDA ratio is a function of the particle size, shape, texture, hardness, and concentration.

The shape of the particles of polyorganosilsesquioxane particles are generally classified as spherical but the surface can be smooth or spiky, or a combination of shapes, depending on the type of manufacturing process. "Spherical" includes particles where the shape of the overall particle is mostly rounded or elliptical in shape but can include particles wherein the surface has bumps or "spikes" extending from the core rounded or elliptical shape. For example, TOSPEARL 145A has a spherical, smooth shape with an mean average particle size of 5.0, while TOSPEARL 150KA has a spherical, "spiky" shape with a mean average particle size of 5.0, both materials commercially available from Momentive Performance Materials, New York, USA.

Figure 2:
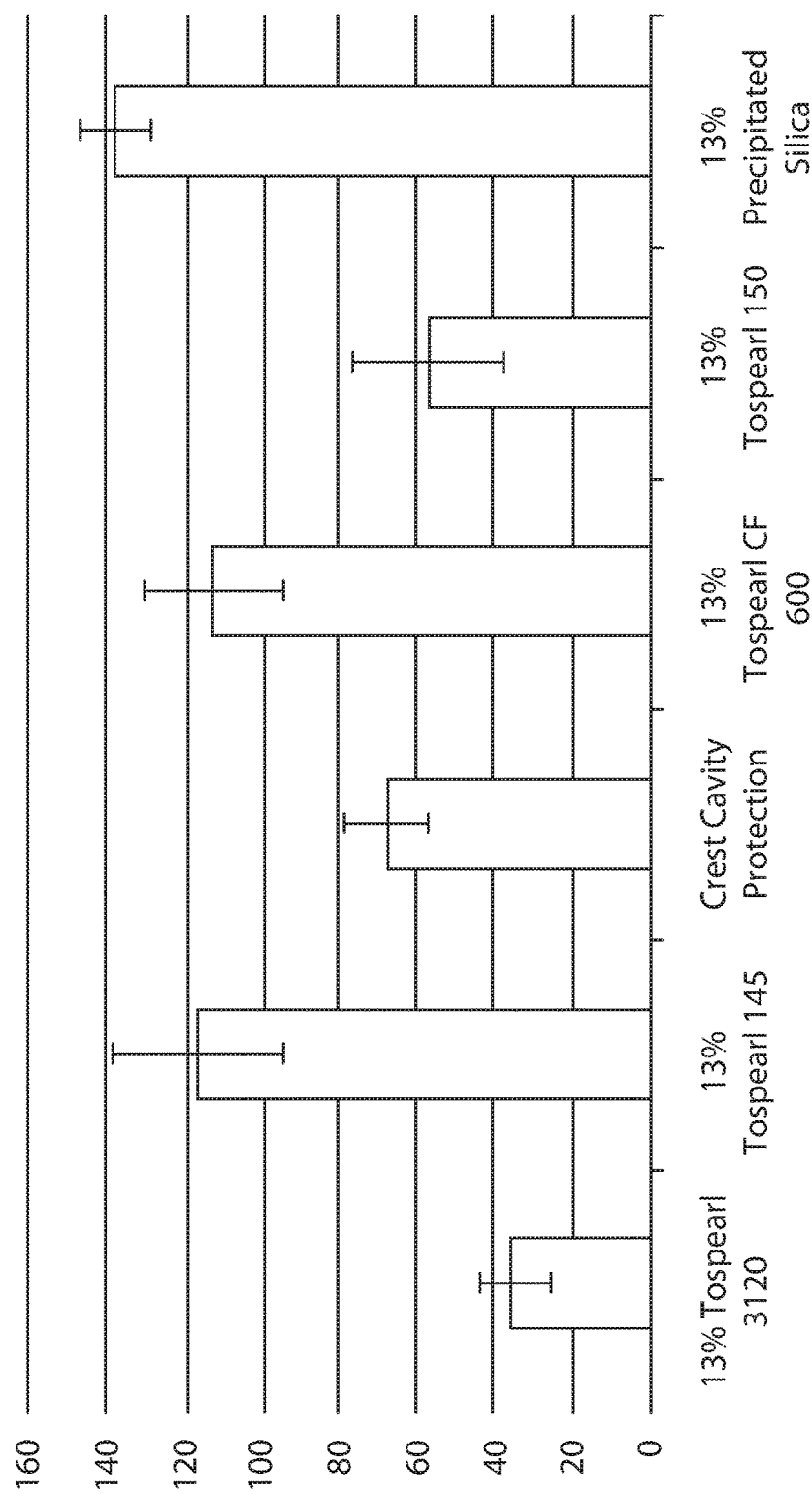
FIG. 2 is a graph of PCR values.

Surprisingly, spherical, smooth surface polymethylsilsesquioxane particles provide better pellicle cleaning ratio "PCR" than the "spiky" spherical particles of a similar mean average particle size as may be seen in Example 1, below and in FIG. 2. In one embodiment, the polyorganosilsesquioxane particles are selected from spherical, smooth surface particles, and mixtures thereof.

The polyorganosilsesquioxane particles, preferably polymethylsilsesquioxane particles, are substantially insoluble in the oral care compositions herein. In one embodiment, the composition is substantially free of volatile carriers capable of solubilizing the organosiloxane particles in the composition. In one embodiment, the composition is substantially free of polysiloxanes. In one embodiment, the composition is substantially free of carbomer. In one embodiment, the composition is substantially free of emollients and waxes.

Oral Care Active

One of the advantages of polyorganosilsesquioxane particles is its compatibility with other materials, particularly materials that are reactive and can lose efficacy such as actives. Because surprisingly, polyorganosilsesquioxane particles do not react as much with actives as compared to precipitated silica and other traditional abrasives, less of the active can be used with the same efficacy. If the active has any potential aesthetic negatives such an unpleasant or strong taste, astringency, staining, or other negative aesthetic, the lower amount of active may be preferred. Additionally, the use of less active for the same or similar efficacy is a cost savings. Alternatively, if the same amount of active as used as traditionally used, the active would have higher efficacy as more of it is available to provide the benefit.

The oral care active herein includes an oxidizing agent and may include additional oral care actives. Oral care actives useful herein include antibacterial agents, antiplaque agents, anticaries agents, antisensitivity agents, antierosion agents, oxidizing agents, anti-inflammatory agents, anticalculus agents, chelating agents, tooth substantive agents, antioxidants, analgesic agents, anesthetic agents, H-1 and H-2 antagonists, antiviral actives, nutrients and mixtures thereof. These materials are described more fully below and a material or ingredient may be categorized as more than one type of materials. Such as an antioxidant may also be an antiplaque and antibacterial active. Examples of suitable actives include stannous fluoride, sodium fluoride, essential oils, mono alkyl phosphates, hydrogen peroxide, CPC, chlorhexidine, Triclosan, and combinations thereof.

In one embodiment, the oral care active is selected from stannous fluoride, sodium fluoride, monofluorophosphate, cetylpyridinium chloride, triclosan, arginine, and mixtures thereof. Mixtures of oral care actives may be used. In one embodiment, the oral care active is selected from one or more of a fluoride ion source, zinc ion source, calcium ion source, phosphate ion source, potassium ion source, strontium ion source, aluminum ion source, magnesium ion source, or combinations thereof. In one embodiment, the oral care active is a mixture of stannous ion source, fluoride ion source, and zinc ion source.

Antibacterial Agent

The oral care active may include an effective amount of an antibacterial agent. The composition may contain from about 0.001% to about 20%, alternatively from about from about 0.1% to about 5%, by weight of the oral care composition, of one or more antibacterial agents.

Antibacterial agents useful herein include chlorhexidine, alexidine, hexetidine, benzalkonium chloride, domiphen bromide, cetylpyridinium chloride (CPC), tetradecylpyridinium chloride (TPC), N-tetradecyl-4-ethylpyridinium chloride (TDEPC), octenidine, bisbiguanides, zinc or stannous ion agents, grapefruit extract, and mixtures thereof. Other antibacterial and antimicrobial agents include: 5-chloro-2-(2,4-dichlorophenoxy)-phenol, commonly referred to as triclosan; 8-hydroxyquinoline and its salts, copper II compounds, including, copper(II) chloride, copper(II) sulfate, copper(II) acetate, copper(II) fluoride and copper(II) hydroxide; phthalic acid and its salts including those disclosed in U.S. Pat. No. 4,994,262, including magnesium monopotassium phthalate; sanguinarine; salicylanilide; iodine; sulfonamides; phenolics; delmopinol, octapinol, and other piperidino derivatives; niacin preparations; nystatin; apple extract; thyme oil; thymol; antibiotics such as augmentin, amoxicillin, tetracycline, doxycycline, minocycline, metronidazole, neomycin, kanamycin, cetylpyridinium chloride, and clindamycin; analogs and salts of the above; methyl salicylate; hydrogen peroxide; metal salts of chlorite; pyrrolidone ethyl cocoyl arginate; lauroyl ethyl arginate monochlorohydrate; and mixtures of all of the above. In another embodiment, the composition comprises phenolic antimicrobial compounds and mixtures thereof.

Other antimicrobial agents include essential oils. Essential oils are volatile aromatic oils which may be synthetic or may be derived from plants by distillation, expression or extraction, and which usually carry the odor or flavor of the plant from which they are obtained. Useful essential oils may provide antiseptic activity. Some essential oils may also act as flavoring agents. Useful essential oils include but are not limited to citra, thymol, menthol, methyl salicylate (wintergreen oil), eucalyptol, carvacrol, camphor, anethole, carvone, eugenol, isoeugenol, limonene, osimen, n-decyl alcohol, citronel, a-salpineol, methyl acetate, citronellyl acetate, methyl eugenol, cineol, linalool, ethyl linalaol, safrola vanillin, spearmint oil, peppermint oil, lemon oil, orange oil, sage oil, rosemary oil, cinnamon oil, pimento oil, laurel oil, cedar leaf oil, gerianol, verbenone, anise oil, bay oil, benzaldehyde, bergamot oil, bitter almond, chiorothymol, cinnamic aldehyde, citronella oil, clove oil, coal tar, *eucalyptus* oil, guaiacol, tropolone derivatives such as hinokitiol, avender oil, mustard oil, phenol, phenyl salicylate, pine oil, pine needle oil, *sassafras* oil, spike lavender oil, storax, thyme oil, tolu balsam, terpentine oil, clove oil, and combinations thereof. In one embodiment the essential oils are selected from thymol, methyl salicylate, eucalyptol, menthol and combinations thereof.

In one embodiment of the present invention, oral care compositions are provided comprising a blend of naturally occurring flavor ingredients or essential oils (EO) containing such flavor ingredients, the blend exhibiting excellent antimicrobial activity and comprising at least two components, a first component selected from acyclic or non-ring structures such as citral, neral, geranial, geraniol and nerol and a second component selected from ring-containing or cyclic structures such as eucalyptol, eugenol and carvacrol. Essential oils may be used to provide the above flavor ingredients including oils of lemongrass, citrus (orange, lemon, lime), citronella, geranium, rose, *eucalyptus*, oregano, bay and clove. Preferred for use herein are natural oils or extracts that have been purified or concentrated to contain mainly the desired component(s).

Other antibacterial agents may be basic amino acids and salts. Other embodiments may comprise arginine.

Anti-Plaque Agent

The oral care active may include an effective amount of an anti-plaque agent. The composition may contain from about 0.001% to about 20%, alternatively from about from about 0.1% to about 5%, by weight of the oral care composition, of one or more anti-plaque agents.

Anti-plaque agents useful herein include stannous salts, copper salts, strontium salts, magnesium salts, copolymers of carboxylated polymers such as GANTREZ or a dimethicone copolyol. The dimethicone copolyol is selected from C12 to C20 alkyl dimethicone copolyols and mixtures thereof. In one embodiment the dimethicone copolyol is cetyl dimethicone copolyol marketed under the Trade Name ABIL EM90. The dimethicone copolyol in one embodiment can be present in a level of from about 0.001% to about 25%, in another embodiment from about 0.01% to about 5%, and in another embodiment from about 0.1% to about 1.5% by weight of the oral composition.

Anti-Caries Agent

The oral care active may include an effective amount of an anti-caries agent. In one embodiment, the anti-caries agent is a fluoride ion source. The fluoride ion may be present in an amount sufficient to give a fluoride ion concentration in the composition at 25° C., and/or in one embodiment can be used at levels of from about 0.0025% to about 5.0% by weight of the composition, alternatively from about 0.005% to about 2.0% by weight of the composition, to provide anticaries effectiveness. Examples of suitable fluoride ion-yielding materials are disclosed in U.S. Pat. Nos. 3,535,421, and 3,678,154. Representative fluoride ion sources include: stannous fluoride, sodium fluoride, potassium fluoride, amine fluoride, sodium monofluorophosphate, zinc fluoride, and mixtures thereof. In one embodiment the oral care composition contains a fluoride source selected from stannous fluoride, sodium fluoride, and mixtures thereof.

The pH of the oral composition may be from about 3 to about 10. The pH is typically measured as a slurry pH by methods known in the industry. Depending upon the actives used in the oral composition, a different pH may be desired. For formulations containing fluoride, it may be desired to have a pH slightly lower than typical dentifrices. Compositions containing polyorganosilsesquioxane particles and fluoride may have a pH of less than about 6.5 or less than about 5.5. The pH may be less than about 5.2 or about 5.0. It may be desired to have a pH of from about 3.5 to about 5 or from about 2.4 to about 4.8. For formulations containing peroxide and polyorganosilsesquioxane particles, the pH may be less than 5.5, alternatively less than 5.0, alternatively less than 4.5. A formulation with peroxide and polyorganosilsesquioxane particles may be from about 3.5 to about 4.0. For formulations comprising polyorganosilsesquioxane particles, stannous, and fluoride, it may be desired to have a pH of less than 5.0. Without being limited by theory, a pH of less than 5.0 may enable more of the SnF3 stannous species to be formed.

Anti-Sensitivity Agents

The oral care active may include an effective amount of an anti-sensitivity agent. The composition may contain from about 0.001% to about 20%, alternatively from about from about 0.1% to about 5%, by weight of the oral care composition, of the anti-sensitivity agent.

Anti-sensitivity agents useful herein include tubule blocking agents and/or desensitivity agents. Tubule blocking agents may be selected from the group consisting of stannous ion source, strontium ion source, calcium ion source, phosphorus ion source, aluminum ion source, magnesium ion source, amino acids, bioglasses, nanoparticulates, polycarboxylates, GANTREZ, and mixtures thereof. The amino acids may be basic amino acids, and a basic amino acid may be arginine. Nanoparticulates may be selected from the group consisting of nanohydroxy apatite, nanotitanium dioxide, nano metal oxides, and mixtures thereof. The desensitivity agent may be a potassium salt selected from the group consisting of potassium fluoride, potassium citrate, potassium nitrate, potassium chloride, and mixtures thereof. Some embodiments may be a method of reducing hypersensitivity of the teeth by administering to a subject in need an oral care composition comprising a polyorganosilsesquioxane particles.

Anti-Erosion Agents

The oral care active may include an effective amount of an anti-erosion agent, such as a stannous ion source. As stated before, one of the advantages of polyorganosilsesquioxane particles is its compatibility with other materials, particularly materials that are reactive and can lose efficacy, such as stannous ions. Because polyorganosilsesquioxane particles do not react as much with stannous as compared to precipitated silica and other traditional abrasives, less of the stannous can be used with the same efficacy. It has been reported that stannous may have potential aesthetic negatives such an unpleasant or strong taste, astringency, staining, or other negative aesthetics that make the stannous containing oral compositions less desirable for consumers.

The stannous ions may be provided from stannous fluoride and/or other stannous salts. Stannous fluoride has been found to help in the reduction of gingivitis, plaque, sensitivity, erosion, and in improved breath benefits. Formulations providing such efficacy typically include stannous levels provided by stannous fluoride and/or other stannous salts ranging from about 50 ppm to about 15,000 ppm stannous ions in the total composition. The stannous ion is present in an amount of from about 1,000 ppm to about 10,000 ppm, in one embodiment from about 3,000 ppm to about 7,500 ppm. Other stannous salts include organic stannous carboxylates, such as stannous acetate, stannous gluconate, stannous oxalate, stannous malonate, stannous citrate, stannous ethylene glycoxide, stannous formate, stannous sulfate, stannous lactate, stannous tartrate, and the like. Other stannous ion sources include, stannous halides such as stannous chlorides, stannous bromide, stannous iodide and stannous chloride dihydride. In one embodiment the stannous ion source is stannous fluoride, in another embodiment stannous chloride dehydrate or trihydrate, or stannous gluconate. The combined stannous salts may be present in an amount of from about 0.001% to about 11%, by weight of the oral care compositions. The stannous salts may, in one embodiment, be present in an amount of from about 0.01% to about 7%, in another embodiment from about 0.1% to about 5%, and in another embodiment from about 1.5% to about 3%, by weight of the oral care composition.

Whitening and Oxidizing Agents

The oral care active may include an effective amount of a whitening or oxidizing agent, generally referred to herein as oxidizing agents. Oxidizing agents useful herein include alkali metal and alkaline earth metal peroxides, metal chlorites, perborates inclusive of mono and tetrahydrates, perphoshates, percarbonates, peroxyacids, and persulfates, such as ammonium, potassium, sodium and lithium persulfates, and combinations thereof. Suitable peroxide compounds include hydrogen peroxide, urea peroxide, calcium peroxide, carbamide peroxide, magnesium peroxide, zinc peroxide, strontium peroxide and mixtures thereof. In one embodiment the peroxide compound is carbamide peroxide. Suitable metal chlorites include calcium chlorite, barium chlorite, magnesium chlorite, lithium chlorite, sodium chlorite, and potassium chlorite. Additional whitening actives may be hypochlorite and chlorine dioxide. In one embodiment the chlorite is sodium chlorite. In another embodiment the percarbonate is sodium percarbonate. In one embodiment the persulfates are oxones. The level of these substances is dependent on the available oxygen or chlorine, respectively, that the molecule is capable of providing to bleach the stain. In one embodiment the whitening agents may be present at levels from about 0.01% to about 40%, in another embodiment from about 0.1% to about 20%, in another embodiment form about 0.5% to about 10%, and in another embodiment from about 4% to about 7%, by weight of the oral care composition.

The oral care active may include an effective amount of an oxidizing agent, such as a peroxide source. A peroxide source may comprise hydrogen peroxide, calcium peroxide, carbamide peroxide, or mixtures thereof. In some embodiments, the peroxide source is hydrogen peroxide. Other peroxide actives can include those that produce hydrogen peroxide when mixed with water, such as percarbonates, e.g., sodium percarbonates. In certain embodiments, the peroxide source may be in the same phase as a stannous ion source. In some embodiments, the composition comprises from about 0.01% to about 20% of a peroxide source, in other embodiments from about 0.1% to about 5%, in certain embodiments from about 0.2% to about 3%, and in another embodiment from about 0.3% to about 2.0% of a peroxide source, by weight of the oral composition. The peroxide source may be provided as free ions, salts, complexed, or encapsulated.

In addition to the other oral care materials detailed herein, certain thickeners and flavoring agents may offer better compatibility with oxidizing agents such as peroxide. For example, in some embodiments, preferred thickening agents may be cross-linked polyvinylpyrrolidone, polyacrylates, alkylated polyacrylates, alkylated cross-linked polyacrylates, polymeric alkylated polyethers, carbomers, alkylated carbomers, gel networks, non-ionic polymeric thickeners, Sepinov EMT 10 (Seppic-hydroxyethyl acrylate/sodium acryloldimethyltaurate copolymer), Pure Thix 1450, 1442, HH (PEG 180 laureth-50/TMMP or Polyether 1-Rockwood Specialties), Structure 2001 (Akzo-Acrylates/Steareth-20 Itaconate copolymer), Structure 3001 (Akzo-Acrylates/Ceteth-20 Itaconate copolymer), Aculyn 28 (Dow Chemical/Rohm and Haas-Acrylates/Beheneth-25 Methacrylate Copolymer), Genopur 3500D (Clariant), Aculyn 33 (Dow Chemical/Rohm and Haas-Acrylates Copolymer), Aculyn 22 (Dow Chemical/Rohm and Haas-Acrylates/Steareth-20 Methacrylate Copolymer), Aculyn 46 (Dow Chemical/Rohm and Haas-PEG-150/Stearyl Alcohol/SMDI Copolymer), A500 (crosslinked carboxymethylcellulose-Hercules), Structure XL (hydroxypropyl starch phosphate-National Starch), and mixtures thereof.

Other suitable thickening agents may include polymeric sulfonic acids such as Aristoflex AVC, AVS, BLV and HMB (Clariant, acryloyldimethyltaurate polymers, copolymers and cross polymers), Diaformer (Clariant, amineoxide methacrylate copolymer), Genapol (Clariant, fatty alcohol polyglycol ether and alkylated polyglycol ethoxylated fatty alcohol), fatty alcohols, ethoxylated fatty alcohols, high molecular weight non-ionic surfactants such as BRIJ 721 (Croda), and mixtures thereof.

Suitable flavoring agents particularly compatible with peroxide include those discussed in US application 2007/0231278. In one embodiment, the flavoring agent includes menthol in combination with at least one secondary cooling agent along with selected traditional flavor components that have been found to be relatively stable in the presence of peroxide. By "stable" herein is meant that the flavor character or profile does not significantly change or is consistent during the life of the product.

The present composition may comprise from about 0.04% to 1.5% total coolants (menthol+secondary coolant) with at least about 0.015% menthol by weight. Typically, the level of menthol in the final composition ranges from about 0.015% to about 1.0% and the level of secondary coolant(s) ranges from about 0.01% to about 0.5%. Preferably, the level of total coolants ranges from about 0.03% to about 0.6%.

Suitable secondary cooling agents or coolants to be used with menthol include a wide variety of materials such as carboxamides, ketals, diols, menthyl esters and mixtures thereof. Examples of secondary coolants in the present compositions are the paramenthan carboxamide agents such as N-ethyl-p-menthan-3-carboxamide, known commercially as "WS-3", N,2,3-trimethyl-2-isopropylbutanamide, known as "WS-23", and others in the series such as WS-5, WS-11, WS-14 and WS-30. Additional suitable coolants include 3-1-menthoxypropane-1,2-diol known as TK-10 manufactured by Takasago; menthone glycerol acetal known as MGA; menthyl esters such as menthyl acetate, menthyl acetoacetate, menthyl lactate known as Frescolat® supplied by Haarmann and Reimer, and monomenthyl succinate under the tradename Physcool from V. Mane. The terms menthol and menthyl as used herein include dextro- and levorotatory isomers of these compounds and racemic mixtures thereof.

Traditional flavor components that have been found to be relatively stable in the presence of peroxide include methyl salicylate, ethyl salicylate, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, cinnamic aldehyde, octanol, octanal, decanol, decanal, phenylethyl alcohol, benzyl alcohol, benzaldehyde, alpha-terpineol, linalool, limonene, citral, vanillin, ethyl vanillin, propenyl guaethol, maltol, ethyl maltol, heliotropin, anethole, dihydroanethole, carvone, oxanone, menthone, β-damascenone, ionone, gamma decalactone, gamma nonalactone, gamma undecalactone, 4-hydroxy-2,5-dimethyl-3(2H)-furanone and mixtures thereof. Generally suitable flavoring agents are those containing structural features and functional groups that are less prone to oxidation by peroxide. These include derivatives of flavor chemicals that are saturated or contain stable aromatic rings or ester groups. Also suitable are flavor chemicals that may undergo some oxidation or degradation without resulting in a significant change in the flavor character or profile. Flavoring agents are generally used in the compositions at levels of from about 0.001% to about 5%, by weight of the composition.

In some embodiments, the pH of the composition may be from about 3.5 to about 5.5, which can provide additional stability for the oxidizing agent. In some embodiments, the composition may further comprise a stannous ion source. In some embodiments, the present invention may provide a method of reducing plaque, gingivitis, sensitivity, oral malodor, erosion, cavities, calculus, and staining by administering to a subject's oral cavity a composition comprising a polyorganosilsesquioxane particles and a peroxide. In some embodiments, the present invention provides a method of reducing plaque, gingivitis, sensitivity, oral malodor, erosion, cavities, calculus, and staining by administering to a subject's oral cavity first a composition not comprising a peroxide, and then a composition comprising a polyorganosilsesquioxane particles and a peroxide. In some embodiments, the composition may be in a single phase. The composition may comprise an oxidizing agent and a chelant The composition may comprise an oxidizing agent and an oral care active.

Anti-Inflammatory Agents

The oral care active may include an effective amount of an anti-inflammatory agent. Such agents include non-steroidal anti-inflammatory (NSAID) agents oxicams, salicylates, propionic acids, acetic acids and fenamates. NSAIDs include ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone, phenylbutazone and acetaminophen. Suitable steroidal anti-inflammatory agents include corticosteroids, such as fluccinolone, and hydrocortisone.

Anticalculus Agent

The oral care active may include an effective amount of an anti-calculus agent, which in one embodiment may be present from about 0.05% to about 50%, by weight of the oral care composition, in another embodiment is from about 0.05% to about 25%, alternatively from about 0.1% to about 15%. The anti-calculus agent may be selected from the group consisting of polyphosphates (including pyrophosphates) and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof; polycarboxylates and salts thereof; carboxy-substituted polymers; and mixtures thereof. In one embodiment, the polymeric polycarboxylates employed herein include those described in U.S. Pat. No. 5,032,386. An example of these polymers that is commercially available is GANTREZ from International Speciality Products (ISP). In one embodiment, the salts are alkali metal or ammonium salts. Polyphosphates are discussed more fully herein as tooth substantive agents. The inorganic polyphosphate salts include alkali metal (e.g. sodium) tripolyphosphate, tetrapolyphosphate, dialkyl metal (e.g. disodium) diacid, trialkyl metal (e.g. trisodium) monoacid, potassium hydrogen phosphate, sodium hydrogen phosphate, and alkali metal (e.g. sodium) hexametaphosphate, and mixtures thereof. The pyrophosphate salts useful in the present invention include, alkali metal pyrophosphates, di-, tri-, and mono-potassium or sodium pyrophosphates, dialkali metal pyrophosphate salts, tetraalkali metal pyrophosphate salts, and mixtures thereof. In one embodiment the pyrophosphate salt is selected from the group consisting of trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof. Polyolefin sulfonates include those wherein the olefin group contains 2 or more carbon atoms, and salts thereof. Polyolefin phosphonates include those wherein the olefin group contains 2 or more carbon atoms. Polyvinylphosphonates include polyvinylphosphonic acid. Diphosphonates and salts thereof include azocycloalkane-2,2-diphosphonic acids and salts thereof, ions of azocycloalkane-2,2-diphosphonic acids and salts thereof, azacyclohexane-2,2-diphosphonic acid, azacyclopentane-2,2-diphosphonic acid, N-methyl-azacyclopentane-2,3-diphosphonic acid, EHDP (ethane-1-hydroxy-1,1,-diphosphonic acid), AHP (azacycloheptane-2,2-diphosphonic acid), ethane-1-amino-1,1-diphosphonate, dichloromethane-diphosphonate, etc. Phosphonoalkane carboxylic acid or their alkali metal salts include PPTA (phosphonopropane tricarboxylic acid), PBTA (phosphonobutane-1,2,4-tricarboxylic acid), each as acid or alkali metal salts. Polyolefin phosphates include those wherein the olefin group contains 2 or more carbon atoms. Polypeptides include polyaspartic and polyglutamic acids.

Chelating Agent

The oral care active may include an effective amount of a chelating agent, also referred to as sequestrants, many of which also have anticalculus activity or tooth substantive activity. Use of chelating agents in oral care products is advantageous for their ability to complex calcium such as found in the cell walls of bacteria, to disrupt plaque and to complex with metallic ions. Chelation of ions, such as iron or copper, helps retard oxidative deterioration of finished products.

In one embodiment, the chelating agent is selected from polyphosphates, polycarboxylates, polyvinylpyrrolidone, polyvinyl alcohol, polymeric polyether, polymeric alkyl phosphate, copolymers of methyl vinyl ether and maleic anhydride, polyphosphonates, sodium alginate, carbonyl diphosphonates; acrylic acid polymers; polyvinyl pyrrolidone, copolymers of vinyl pyrrolidone with carboxylates, and mixtures thereof.

The amount of chelating agent in the compositions will depend on the chelating agent used and typically will be from at least about 0.1% to about 20%, preferably from about 0.5% to about 10% and more preferably from about 1.0% to about 7%.

Suitable chelating agents include soluble phosphate compounds, such as phytates, linear polyphosphates having two or more phosphate groups, and other polyphosphorylated compounds, all discussed more fully below as tooth substantive agents.

Still other phosphate compounds useful herein as chelating agents are the surface active organophosphate compounds described below useful as tooth substantive agents including organic phosphate mono-, di- or triesters.

Chelating agents useful herein include the anionic polymeric polycarboxylates in the form of their free acids or partially or preferably fully neutralized water soluble alkali metal (e.g. potassium and preferably sodium) or ammonium salts. Examples include 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as GANTREZ® AN 139 (M.W. 500,000), AN 119 (M.W. 250,000) and S-97 Pharmaceutical Grade (M.W. 70,000), of GAF Chemicals Corporation.

Other operative polymeric polycarboxylates include the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates are disclosed in U.S. Pat. No. 4,138,477, Feb. 6, 1979 to Gaffar and U.S. Pat. No. 4,183,914, Jan. 15, 1980 to Gaffar et al. and include copolymers of maleic anhydride with styrene, isobutylene or ethyl vinyl ether; polyacrylic, polyitaconic and polymaleic acids; and sulfoacrylic oligomers of M.W. as low as 1,000 available as Uniroyal ND-2.

Other suitable chelants include polycarboxylic acids and salts thereof described in U.S. Pat. No. 5,015,467 to Smitherman U.S. Pat. Nos. 5,849,271 and 5,622,689 both to Lukacovic; such as tartaric acid, citric acid, gluconic acid, malic acid; succinic acid, disuccinic acid and salts thereof, such as sodium or potassium gluconate and citrate; citric acid/alkali metal citrate combination; disodium tartrate; dipotassium tartrate; sodium potassium tartrate; sodium hydrogen tartrate; potassium hydrogen tartrate; acid or salt form of sodium tartrate monosuccinate, potassium tartrate disuccinate, and mixtures thereof. In some embodiments, there may be mixtures or combinations of chelating agents.
Tooth Substantive Agent The oral care active may include an effective amount of a tooth substantive agent. For purposes of this application, tooth substantive agents are included as chelants also. Suitable agents may be polymeric surface active agents (PMSA's), including polyelectrolytes, more specifically anionic polymers.

Without being limited by theory, it is believed that PMSA's provide a stain prevention benefit because of their reactivity or substantivity to mineral or tooth surfaces, resulting in desorption of portions of undesirable adsorbed pellicle proteins, in particular those associated with binding color bodies that stain teeth, calculus development and attraction of undesirable microbial species. The retention of these PMSA's on teeth can also prevent stains from accruing due to disruption of binding sites of color bodies on tooth surfaces.

The PMSA's include any agent which will have a strong affinity for the tooth surface, deposit a polymer layer or coating on the tooth surface and produce the desired surface modification effects. Suitable examples of such polymers are polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate) and poly(vinyl benzyl chloride); polycarboxylates and carboxy-substituted polymers; and mixtures thereof. Suitable polymeric mineral surface active agents include the carboxy-substituted alcohol polymers described in U.S. Pat. Nos. 5,292,501; 5,213,789, 5,093,170; 5,009,882; and 4,939,284; all to Degenhardt et al. and the diphosphonate-derivatized polymers in U.S. Pat. No. 5,011,913 to Benedict et al; the synthetic anionic polymers including polyacrylates and copolymers of maleic anhydride or acid and methyl vinyl ether (e.g., GANTREZ®), as described, for example, in U.S. Pat. No. 4,627,977, to Gaffar et al. A preferred polymer is diphosphonate modified polyacrylic acid. Polymers with end or side chain phosphate or phosphonate functions are preferred although other polymers with mineral binding activity may prove effective depending upon adsorption affinity.

Additional examples of suitable phosphonate containing polymeric mineral surface active agents include the geminal diphosphonate polymers disclosed as anticalculus agents in U.S. Pat. No. 4,877,603 to Degenhardt et al; phosphonate group containing copolymers disclosed in U.S. Pat. No. 4,749,758 to Dursch et al. and in GB 1,290,724 (both assigned to Hoechst) suitable for use in detergent and cleaning compositions; and the copolymers and cotelomers disclosed as useful for applications including scale and corrosion inhibition, coatings, cements and ion-exchange resins in U.S. Pat. No. 5,980,776 to Zakikhani et al. and U.S. Pat. No. 6,071,434 to Davis et al. Additional polymers include the water-soluble copolymers of vinylphosphonic acid and acrylic acid and salts thereof disclosed in GB 1,290,724 wherein the copolymers contain from about 10% to about 90% by weight vinylphosphonic acid and from about 90% to about 10% by weight acrylic acid, more particularly wherein the copolymers have a weight ratio of vinylphosphonic acid to acrylic acid of 70% vinylphosphonic acid to 30% acrylic acid; 50% vinylphosphonic acid to 50% acrylic acid; or 30% vinylphosphonic acid to 70% acrylic acid. Other suitable polymers include the water soluble polymers disclosed by Zakikhani and Davis prepared by copolymerizing diphosphonate or polyphosphonate monomers having one or more unsaturated C=C bonds (e.g., vinylidene-1,1-diphosphonic acid and 2-(hydroxyphosphinyl)ethylidene-1,1-diphosphonic acid), with at least one further compound having unsaturated C=C bonds (e.g., acrylate and methacrylate monomers). Suitable polymers include the diphosphonate/acrylate polymers supplied by Rhodia under the designation ITC 1087 (Average MW 3000-60,000) and Polymer 1154 (Average MW 6000-55,000).

One preferred PMSA is a polyphosphate. Although pyrophosphates (n=2) are technically polyphosphates, the polyphosphates desired are those having around three or more phosphate groups so that surface adsorption at effective concentrations produces sufficient non-bound phosphate functions, which enhance the anionic surface charge as well as hydrophilic character of the surfaces. The inorganic polyphosphate salts desired include tripolyphosphate, tetrapolyphosphate and hexametaphosphate, among others. Polyphosphates larger than tetrapolyphosphate usually occur as amorphous glassy materials. Preferred in the present compositions are the linear polyphosphates having the formula:

wherein X is sodium, potassium or ammonium and n averages from about 3 to about 125. Preferred polyphosphates are those having n averaging from about 6 to about 21, such as those commercially known as Sodaphos (n≈6), Hexaphos (n≈13), and Glass H (n≈21) and manufactured by FMC Corporation and Astaris. These polyphosphates may be used alone or in combination. Polyphosphates are susceptible to hydrolysis in high water formulations at acid pH, particularly below pH 5. Thus it is preferred to use longer-chain polyphosphates, in particular Glass H with an average chain length of about 21. It is believed such longer-chain polyphosphates when undergoing hydrolysis produce shorter-chain polyphosphates which are still effective to deposit onto teeth and provide a stain preventive benefit.

Also useful as tooth substantive agents are nonpolymeric phosphate compounds, in particular polyphosphorylated inositol compounds such as phytic acid, myo-inositol pentakis(dihydrogen phosphate); myo-inositol tetrakis(dihydrogen phosphate), myo-inositol trikis(dihydrogen phosphate), and an alkali metal, alkaline earth metal or ammonium salt thereof. Preferred herein is phytic acid, also known as myo-inositol 1,2,3,4,5,6-hexakis (dihydrogen phosphate) or inositol hexaphosphoric acid, and its alkali metal, alkaline earth metal or ammonium salts. Herein, the term "phytate" includes phytic acid and its salts as well as the other polyphosphorylated inositol compounds.

Other surface active phosphate compounds useful as tooth substantive agents include organophosphates such as phosphate mono-, di- or triesters such as described in commonly assigned application published as US20080247973A1. Examples include mono- di- and tri-alkyl and alkyl (poly) alkoxy phosphates such as dodecyl phosphate, lauryl phosphate; laureth-1 phosphate; laureth-3 phosphate; laureth-9 phosphate; dilaureth-10 phosphate; trilaureth-4 phosphate; C12-18 PEG-9 phosphate and salts thereof. Many are commercially available from suppliers including Croda; Rhodia; Nikkol Chemical; Sunjin; Alzo; Huntsman Chemical; Clariant and Cognis. Some preferred agents are polymeric, for example those containing repeating alkoxy groups as the polymeric portion, in particular 3 or more ethoxy, propoxy isopropoxy or butoxy groups.

Additional suitable polymeric organophosphate agents include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol) phosphate, PEG cyclodextrin phosphate, PEG sorbitan phosphate, PEG alkyl sorbitan phosphate, and PEG methyl glucoside phosphate.

Additional suitable non-polymeric phosphates include alkyl mono glyceride phosphate, alkyl sorbitan phosphate, alkyl methyl glucoside phosphate, alkyl sucrose phosphates.

Other useful tooth substantive agents include siloxane polymers functionalized with carboxylic acid groups, such as disclosed in disclosed in U.S. Pat. Nos. 7,025,950 and 7,166,235 both assigned to The Procter & Gamble Co. Also useful as tooth substantive agents are water-soluble or water-dispersible polymeric agents prepared by copolymerizing one or a mixture of vinyl pyrrolidone (VP) monomers with one or a mixture of alkenyl carboxylate (AC) monomers, specifically C2-C12 alkenyl esters of saturated straight- or branched-chain C1-C19 alkyl carboxylic acids described in commonly assigned U.S. Pat. No. 6,682,722. Examples include copolymers of vinyl pyrrolidone with one or a mixture of vinyl acetate, vinyl propionate, or vinyl butyrate. Preferred polymers have an average molecular weight ranging from about 1,000 to about 1,000,000, preferably from 10,000 to 200,000, even more preferably from 30,000 to 100,000.

The amount of tooth substantive agent will typically be from about 0.1% to about 35% by weight of the total oral care composition. In dentifrice formulations, the amount is preferably from about 2% to about 30%, more preferably from about 5% to about 25%, and most preferably from about 6% to about 20%.

Analgesic and Anesthetic Agents

The oral care active may include an effective amount of an anti-pain or desensitizing agents. Such agents may include strontium chloride; potassium nitrate; sodium fluoride; sodium nitrate; acetanilide; phenacetin; acertophan; thiorphan; spiradoline; aspirin; codeine; thebaine; levorphenol; hydromorphone; oxymorphone; phenazocine; fentanyl; buprenorphine; butaphanol; nalbuphine; pentazocine; natural herbs, such as gall nut; *Asarum*; Cubebin; Galanga; scutellaria; Liangmianzhen; and Baizhi. Anesthetic agents, or topical analgesics, such as acetaminophen, sodium salicylate, trolamine salicylate, lidocaine and benzocaine may also be present. These analgesic actives are described in detail in Kirk-Othmer, *Encyclopedia of Chemical Technology*, Fourth Edition, Volume 2, Wiley-Interscience Publishers (1992), pp. 729-737.

H-1 and H-2 Antagonists and Antiviral Actives

The oral care active may include an effective amount of selective H-1 and H-2 antagonists including compounds disclosed in U.S. Pat. No. 5,294,433. The stannous salts that may be used in the present invention would include organic stannous carboxylates and inorganic stannous halides. While stannous fluoride may be used, it is typically used only in combination with another stannous halide or one or more stannous carboxylates or another therapeutic agent.

Nutrients

The oral care active may include an effective amount of a nutrient. Nutrients include minerals, vitamins, oral nutritional supplements, enteral nutritional supplements, and mixtures thereof. Useful minerals include calcium, phosphorus, zinc, manganese, potassium and mixtures thereof. Vitamins can be included with minerals or used independently. Suitable vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Oral nutritional supplements include amino acids, lipotropics, fish oil, and mixtures thereof. Amino acids include, but are not limited to L-Tryptophan, L-Lysine, Methionine, Threonine, Levocarnitine or L-carnitine and mixtures thereof. Lipotropics include, but are not limited to, choline, inositol, betaine, linoleic acid, linolenic acid, and mixtures thereof. Fish oil contains large amounts of Omega-3 (N-3) polyunsaturated fatty acids, eicosapentaenoic acid and docosahexaenoic acid. Enteral nutritional supplements include, but are not limited to, protein products, glucose polymers, corn oil, safflower oil, medium chain triglycerides.

Additional Actives

Additional actives suitable for use in the present invention may include, but are not limited to, insulin, steroids, herbal and other plant derived remedies. Additionally, anti-gingivitis or gum care agents known in the art may also be included. Components which impart a clean feel to the teeth may optionally be included. These components may include, for example, baking soda or Glass-H. Combinations of the materials listed above may be used, for instance, an antimicrobial and an anti-inflammatory agent may be combined in a single dentifrice composition to provide combined effectiveness.

Surfactants

The compositions herein may include a surfactant. The surfactant may be selected from anionic, nonionic, amphoteric, zwitterionic, cationic surfactants, or mixtures thereof. The oral care composition may include a surfactant at a level of from about 0.1% to about 50%, from about 0.025% to about 9%, from about 0.05% to about 5%, from about 0.1% to about 2.5%, from about 0.5% to about 2%, or from about 0.1% to about 1% by weight of the total composition.

Examples of anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Examples of other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976.

Cationic surfactants useful in the present invention include derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. Preferred compounds are the quaternary ammonium fluorides described in U.S. Pat. No. 3,535,421, Oct. 20, 1970, to Briner et al., where said quaternary ammonium fluorides have detergent properties.

Nonionic surfactants that can be used in the compositions of the present invention include compounds produced by the condensation of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, acids, and esters, long chain tertiary amine oxides, long chain tertiary phosphine oxides, long chain dialkyl sulfoxides and mixtures of such materials.

Zwitterionic synthetic surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

Suitable betaine surfactants are disclosed in U.S. Pat. No. 5,180,577 to Polefka et al., issued Jan. 19, 1993. Typical alkyl dimethyl betaines include decyl betaine or 2-(N-decyl-N,N-dimethylammonio) acetate, coco betaine or 2-(N-coc-N, N-dimethyl ammonio) acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice are preferably the cocoamidopropyl betaine and, more preferably, the lauramidopropyl betaine.

In one embodiment, the composition may comprise polyorganosilsesquioxane particles and be essentially free of SLS. Essentially free means that there is less than about 0.01%, by weight of the composition, of the material.

Orally-Acceptable Carrier

The carrier for the components of the present compositions may be any orally-acceptable vehicle suitable for use in the oral cavity. The orally-acceptable carrier includes materials such as buffering agents, secondary abrasive materials, alkali metal bicarbonate salts, thickening agents, gel networks, humectants, water, surfactants, titanium dioxide, flavor agents, coolants, sweetening agents, coloring agents, other suitable materials, and mixtures thereof. The composition may include from about 0.001% to about 90%, alternatively from about 0.01% to about 50%, alternatively from about 0.1% to about 30%, by weight of the oral care composition, of the orally acceptable carrier.

Buffering Agents

The oral care compositions herein may include an effective amount of a buffering agent. Buffering agents, as used herein, refer to agents that can be used to adjust the pH of the dentifrice compositions to a range of about pH 3.0 to about pH 10. The buffering agents include alkali metal hydroxides, ammonium hydroxide, organic ammonium compounds, carbonates, sesquicarbonates, borates, silicates, phosphates, imidazole, and mixtures thereof. Specific buffering agents include monosodium phosphate, trisodium phosphate, sodium benzoate, benzoic acid, sodium hydroxide, potassium hydroxide, alkali metal carbonate salts, sodium carbonate, imidazole, pyrophosphate salts, sodium gluconate, lactic acid, sodium lactate, citric acid, and sodium citrate.

Secondary Abrasive

The oral care compositions herein may further include from about 0.1% to about 60%, alternatively from about 1% to about 50%, alternatively from about 2% to about 40%, alternatively from about 4% to about 30%, alternatively from about 5% to about 25%, by weight of the composition, of one or more secondary abrasives or mixtures thereof.

Examples of secondary abrasive materials useful herein include, precipitated silica, fused silica, calcium carbonate, dicalcium phosphate dihydrate, phosphates (including orthophosphates), pyrophosphates, perlite, pumice, nanodiamonds, surface treated and de-hydrated precipitated silica, rice hull silica, silica gels, aluminas, polymetaphosphates, other inorganic particulates, and mixtures thereof. Examples of secondary abrasive materials useful herein include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962. In one embodiment, the composition includes from about 2% to about 40%, alternatively from about 3% to about 30%, by weight of the composition, of polyorganosilsesquioxane particles and from about 2% to about 40%, alternatively from about 3% to about 30%, by weight of the composition, of a secondary abrasive.

In one embodiment, the composition includes from about 2% to about 40%, alternatively from about 3% to about 30%, by weight of the composition, of polyorganosilsesquioxane particles and from about 2% to about 40%, alternatively from about 3% to about 30%, by weight of the composition, of a secondary abrasive. In one embodiment, the secondary abrasive is selected from precipitated silica, calcium pyrophosphate, and mixtures thereof.

The total abrasive in the compositions described herein is generally present at a level of from about 5% to about 70%, by weight of the composition. Preferably, dentifrice compositions contain from about 5% to about 50% of total abrasive, by weight of the composition. In one embodiment, the ratio of secondary abrasive to polyorganosilsesquioxane particles is greater than about 2 to 1, alternatively, greater than about 10 to 1, alternatively about 1 to 1. In one embodiment, the composition containing a mixture of abrasives may have a PCR of at least about 80, about 100, or about 120, and/or an RDA of less than about 125 or less than about 150 or less than about 250.

Thickening Agents

The oral care compositions herein may include one or more thickening agents, such as a polymeric thickener. Thickening agents may be used in an amount from about 0% to about 15%, or from about 0.01% to about 10%, or from about 0.1% to about 5%, by weight of the total oral composition. Suitable thickening agents include carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Other thickeners may include alkylated polyacrylates, alkylated cross-linked polyacrylates, or gel networks. Thickening agents can include polymeric polyether compounds, e.g., polyethylene or polypropylene oxide (M.W. 300 to 1,000,000), capped with alkyl or acyl groups containing 1 to about 18 carbon atoms.

Copolymers of lactide and glycolide monomers, the copolymer having the molecular weight in the range of from about 1,000 to about 120,000 (number average), are useful for delivery of actives into the periodontal pockets or around the periodontal pockets as a "subgingival gel carrier." These polymers are described in U.S. Pat. Nos. 5,198,220; 5,242,910; and 4,443,430.

The thickening agent may be selected from the group consisting of clay, laponite, and mixtures thereof. In one embodiment, the composition may further comprise a thickening agent selected from the group consisting of carboxyvinyl polymers, carrageenan, hydroxyethyl cellulose, water soluble salts of cellulose ethers such as sodium carboxymethylcellulose, cross-linked carboxymethylcellulose, sodium hydroxyethyl cellulose, cross-linked starch, natural gums such as gum karaya, xanthan gum, gum arabic, and gum tragacanth, magnesium aluminum silicate, silica, alkylated polyacrylates, alkylated cross linked polyacrylates, and mixtures thereof.

Other possible thickeners include carbomers, hydrophobically modified carbomers, carboxymethyl cellulose, cetyl/stearyl alcohol, sodium alginate, gellan gum, acylated gellan gum, sodium hydroxypropyl starch phosphate, microcrystalline cellulose, micro fibrous cellulose, crosslinked polyvinyl pyrrolidone, cetyl hydroxyethyl cellulose, crosslinked sodium acryloyl methyl propane sulfonic acid and copolymers, and mixtures thereof. Carbomers are commercially available from B.F. Goodrich as the Carbopol® series. Particularly the carbopols include Carbopol 934, 940, 941, 956, and mixtures thereof.

The viscosity of the composition at the time it is made may remain the viscosity of the composition, or, stated differently, the composition may have a stable viscosity. For the viscosity to be considered stable, typically the viscosity changes no more than about 5% after 30 days. In some embodiments, the viscosity of the composition does not change by more than about 5% after about 30 days, by more than about 10% after about 30 days, by more than about 20% after about 30 days, or by more than about 50% after about 90 days. Because the problem of unstable viscosity over time is more pronounced in formulations with low water amounts, in some embodiments, the compositions of the present invention may contain less than about 20% total water, or less than about 10% total water.

Gel Network

The oral care compositions herein may include a gel network. Gel networks useful in oral care compositions are described in more detail in U.S. Pat. No. 8,216,552 and Patent Applications, 2008/0081023 and 2009/0246151, all assigned to the Procter & Gamble Company. The gel network may include a fatty amphiphile, surfactant, and a solvent. In one embodiment, the composition includes a gel network and contains from about 0.05% to about 30%, alternatively from about 0.1% to about 20%, alternatively from about 0.5% to about 10%, by weight of the oral composition of a fatty amphiphile; from about 0.01% to about 15%, alternatively from about 0.1% to about 10%, alternatively from about 0.3% to about 5%, by weight of the oral composition, of the surfactant; and at least about 0.05% of a solvent, alternatively from about 0.1% to about 99%, from about 0.5% to about 95%, or from about 1% to about 90%, by weight of the composition, of the solvent.

In one embodiment, the fatty amphiphile is selected from cetyl alcohol, stearyl alcohol, and mixtures thereof. In one embodiment, the surfactant is selected from anionic, zwitterionic, amphoteric, cationic, and nonionic surfactants. In one embodiment, anionic surfactants such as sodium lauryl sulfate, are preferred. Suitable solvents for the present invention include water, edible polyhydric alcohols such as glycerin, diglycerin, triglycerin, sorbitol, xylitol, butylene glycol, erythritol, polyethylene glycol, propylene glycol, and combinations thereof. In one embodiment, the solvent is selected from sorbitol, glycerin, water, and combinations thereof.

Humectants

The compositions herein may include from about 0.1% to about 99%, from about 0.5% to about 95%, or from about 1% to about 90%, by weight of the composition, of a humectant. Suitable humectants for the present invention include water, edible polyhydric alcohols such as glycerin, sorbitol, xylitol, butylene glycol, polyethylene glycol, propylene glycol, and combinations thereof. In one embodiment, the humectant is selected from sorbitol, glycerin, water, and combinations thereof.

Water

The compositions herein may include from about 10% to about 99%, by weight of the composition of water. In one embodiment, the composition includes from about 30% to about 80%, alternatively from about 30% to about 70%, alternatively from about 30% to about 50%, by weight of the composition, of water. In one embodiment, the composition includes less than 20% water.

Flavoring Agents and Coolants

The compositions herein may include from about 0.001% to about 5%, alternatively from about 0.01% to about 4%, alternatively from about 0.1% to about 3%, alternatively from about 0.5% to about 2%, by weight of the oral care composition, of a flavoring agent. Flavoring agents useful herein include oil of wintergreen, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, cranberry, chocolate, green tea, and mixtures thereof. The essential oils may also be included as flavoring agents and are described above in the discussion of antibacterial agents. Coolants may also be used herein. Coolants suitable for the present compositions include the paramenthan carboxyamide agents such as N-ethyl-p-menthan-3-carboxamide (known commercially as WS-3, WS-23, WS-5), MGA, TK-10, Physcool, and mixtures thereof. Salivating agents, warming agents, numbing agents, and other optional materials can be used to deliver a signal while the oral composition is being used.

Some embodiments may comprise a TRPV1 activator, a transient receptor potential vanilloid receptor 1 activator, which is a ligand-gated, non-selective cation channel preferentially expressed on small-diameter sensory neurons and detects noxious as well as other substances. In one embodiment, the TRPV1 activator comprises vanillyl butyl ether, zingerone, capsaicin, capsiate, shoagol, gingerol, piperine, or a combination thereof. In one embodiment, a TRPV1 activator will be added in an amount of about 0.0001% to about 0.25% by weight of the oral care composition.

Sweetener

The oral care compositions herein may include a sweetening agent. These include sweeteners such as saccharin, dextrose, sucrose, lactose, xylitol, maltose, levulose, aspartame, sodium cyclamate, D-tryptophan, dihydrochalcones, acesulfame, sucralose, neotame, and mixtures thereof. Sweetening agents are generally used in oral compositions at levels of from about 0.005% to about 5%, by weight of the composition.

Coloring Agents

The oral care compositions herein may include a coloring agent. The coloring agent may be in the form of an aqueous solution, preferably 1% coloring agent in a solution of water. Pigments, pealing agents, filler powders, talc, mica, magnesium carbonate, calcium carbonate, bismuth oxychloride, zinc oxide, and other materials capable of creating a visual change to the dentifrice compositions may also be used. Color solutions and other agents generally comprise from about 0.01% to about 5%, by weight of the composition. Titanium dioxide may also be added to the present composition. Titanium dioxide is a white powder which adds opacity to the compositions. Titanium dioxide generally comprises from about 0.25% to about 5%, by weight of the composition.

The composition may be essentially free of surfactant, fluoride, and/or any one or more oral care actives. In one embodiment, the compositions herein are free of one or more of the following: enzymes, colorant particles, solvents capable of solubilizing the polyorganosilsesquioxane particles, colorant particles, and/or triclosan.

Method of Use

The present invention also relates to methods for cleaning and polishing teeth. The method of use herein comprises contacting a subject's dental enamel surfaces and oral mucosa with the oral compositions according to the present invention. The method of treatment may be by brushing with a dentifrice or rinsing with a dentifrice slurry or mouthrinse. Other methods include contacting the topical oral gel, mouthspray, toothpaste, dentifrice, tooth gel, tooth powders, tablets, subgingival gel, foam, mouse, chewing gum, lipstick, sponge, floss, petrolatum gel, or denture product or other form with the subject's teeth and oral mucosa. Depending on the embodiment, the oral composition may be used as frequently as a toothpaste, or may be used less often, for example, weekly, or used by a professional in the form of a prophy paste or other intensive treatment.

EXAMPLES

The following examples and descriptions further clarify embodiments within the scope of the present invention. These examples are given solely for the purpose of illustration and are not to be construed as limitations of the present invention as many variations thereof are possible without departing from the spirit and scope.

Example I

Examples 1A-1E are dentifrice compositions that may be suitably prepared by conventional methods chosen by the formulator and illustrate dentifrice compositions containing polymethylsilsesquioxane particles and hydrogen peroxide according to the present invention. The PCR and RDA values for each formulation were determined using the methodology disclosed herein and reported below each formulation in Table 2.

All of these compositions exhibited good cleaning efficacy.

TABLE 2

| Material | 1A Wt. % | 1B Wt. % | 1C Wt. % | 1D Wt. % | 1E Wt. % |
|---|---|---|---|---|---|
| LANETTE W* | 14.723 | 12.733 | 12.548 | 10.544 | 12.548 |
| Sodium lauryl sulfate powder | 1.840 | 1.592 | 1.569 | 1.318 | 1.569 |
| Water | 57.053 | 49.342 | 48.624 | 40.858 | 48.624 |
| Percent of Gel Network in formula | 73.616 | 63.667 | 62.741 | 52.72 | 62.741 |

TABLE 2-continued

| Material | 1A Wt. % | 1B Wt. % | 1C Wt. % | 1D Wt. % | 1E Wt. % |
|---|---|---|---|---|---|
| Sodium monofluorophosphate | | | 1.140 | 1.140 | 1.140 |
| Sodium fluoride | 0.243 | 0.243 | | | |
| SODIUM ACID PYROPHOSPHATE | 0.300 | 0.300 | 0.300 | 0.300 | 0.300 |
| Disodium phosphate | 0.200 | 0.200 | 0.200 | 0.200 | 0.200 |
| Sucralose | 0.250 | 0.250 | 0.250 | 0.250 | 0.250 |
| Calcium Pyrophosphate (PRAYON) | | | 20.000 | 25.000 | 5.000 |
| TOSPEARL CF 600 | 15.000 | 25.000 | 5.000 | 10.000 | 20.000 |
| Flavor | 1.500 | 1.500 | 1.500 | 1.500 | 1.500 |
| Phosphoric Acid | 0.320 | 0.270 | 0.300 | 0.320 | 0.300 |
| Hydrogen peroxide (35% soln) | 8.570 | 8.570 | 8.570 | 8.570 | 8.570 |
| Total => | 100.000 | 100.000 | 100.000 | 100.000 | 100.000 |
| target pH = 4.5 | 4.5 | 4.5 | 4.5 | 4.5 | 4.5 |
| RDA Value | 71 | 72 | 84 | 90 | 76 |
| Standard Deviation | 9 | 9 | 9 | 9 | 9 |
| PCR Value | 95 | 86 | 132 | 125 | 108 |
| Standard Deviation | 7 | 7 | 6 | 6 | 7 |
| Cleaning Efficacy (PCR/RDA) | 1.3 | 1.2 | 1.6 | 1.4 | 1.4 |

LANETTE W is a mixture of cetyl and stearyl alcohol (50:50) with sodium lauryl sulfate (approx. ratio of 90:10) commercially available from Cognis/BASF, located in Germany.
TOSPEARL materials commercially available from Momentive, New Jersey, USA.

Example II

Examples 2F-2K are dentifrice compositions that may be suitably prepared by conventional methods chosen by the formulator. Examples 2G through 2J illustrate dentifrice compositions containing polymethylsilsesquioxane particles and hydrogen peroxide according to the present invention. Example 2F is a comparative example containing no abrasive. Example 2K is a comparative example containing a precipitated silica abrasive commercially available from Huber.

Table 3, below, shows the particle size of the TOSPEARL materials used, as determined by using the methodology set forth herein with a Malvern 2000 (PS-3 Hydro2000SN; Model APA 2000).

The PCR values for each formulation were determined using the methodology disclosed herein and reported below each formulation in Table 4. FIG. 2 is a graph of the PCR values for formulations 2F-2K.

As may be seen from the data below, the compositions containing polymethylsilsesquioxane particles with an average particle size of about 4.2 and smooth surface (TOSPEARL 145A and CF600) exhibited PCR results close to that of precipitated silica. The spiky surface TOSPEARL 150KA and larger particle size TOSPEARL 3120 provided cleaning, but to a lesser extent.

TABLE 3

| Sample Name | Result transform type | D [4, 3] - Volume weighted mean | d (0.1) | d (0.5) | d (0.9) |
|---|---|---|---|---|---|
| TOSPEARL CF600 | Volume | 4.2 | 2.9 | 4.1 | 5.6 |
| TOSPEARL 145A | Volume | 4.2 | 2.9 | 4.1 | 5.7 |
| TOSPEARL 150KA | Volume | 5.0 | 2.9 | 4.8 | 7.5 |
| TOSPEARL 3120 | Volume | 13.2 | 6.1 | 12.9 | 21.3 |

TABLE 4

| | 2F Wt. % | 2G Wt. % | 2H Wt. % | 2I Wt. % | 2J Wt. % | 2K Wt. % |
|---|---|---|---|---|---|---|
| LANETTE W* | 15.000 | 15.000 | 15.000 | 15.000 | 15.000 | 15.000 |
| Sodium lauryl sulfate powder | 1.875 | 1.875 | 1.875 | 1.875 | 1.875 | 1.875 |
| Water | 58.125 | 58.125 | 58.125 | 58.125 | 58.125 | 58.125 |
| Sodium fluoride | 0.243 | 0.243 | 0.243 | 0.243 | 0.243 | 0.243 |
| Sucralose | 0.200 | 0.200 | 0.200 | 0.200 | 0.200 | 0.200 |
| Flavor | 1.000 | 1.000 | 1.000 | 1.000 | 1.000 | 1.000 |
| SODIUM ACID PYROPHOSPHATE | 0.300 | 0.300 | 0.300 | 0.300 | 0.300 | 0.300 |
| Disodium phosphate | 0.300 | 0.200 | 0.200 | 0.200 | 0.300 | 0.200 |
| Precipitated Silica* Z-109 | | | | | | 13.000 |
| TOSPEARL 145A* | | 13.000 | | | | |
| TOSPEARL 3120* | | | 13.000 | | | |
| TOSPEARL CF 600* | | | | 13.000 | | |
| TOSPEARL 150KA* | | | | | 13.000 | |
| Hydrogen peroxide (35% soln) | 8.570 | 8.570 | 8.570 | 8.570 | 8.570 | 8.570 |
| Phosphoric Acid (estimated) | 0.330 | 0.420 | 0.230 | 0.320 | 0.380 | 0.430 |
| Water q.s. | 89.057 | 76.067 | 76.257 | 76.167 | 76.007 | 79.057 |
| Total => | 100.000 | 100.000 | 100.000 | 100.000 | 100.000 | 100.000 |
| pH Target => | 4.5 | 4.5 | 4.5 | 4.5 | 4.5 | 4.5 |
| PCR Value | 68.49 | 116.9 | 35.1 | 112.37 | 56.98 | 137.94 |
| Standard Deviation | 10.84 | 21.7 | 9.39 | 18.18 | 19.42 | 9.27 |

LANETTE W is a mixture of cetyl and stearyl alcohol (50:50) with sodium lauryl sulfate (approx. ratio of 90:10) commercially available from Cognis/BASF, located in Germany.
TOSPEARL materials commercially available from Momentive, New Jersey, USA.
Precipitated silica ZEODENT 109 available from Huber.

Example III

Example III—Peroxide Stability

Examples 3A-3E in Table 7 are dentifrice compositions that may be suitably prepared by conventional methods chosen by the formulator. Examples 3B-3E illustrate dentifrice compositions containing polymethylsilsesquioxane particles and peroxide according to the present invention. Example 3A is a comparative example containing no abrasive.

The formulation stability of peroxide, over time was determined using the methodology set forth below and the results tabulated in Table 6. As shown below in Table 6, formulations 3B-3E exhibited good peroxide stability after storage at 40° C. for 4, 8 and 12 weeks.

For comparison, the peroxide stability of a similar formulation containing precipitated silica in place of the polymethylsilsesquioxane is shown in Table 8 for the formulation 3F shown in Table 7 (below). As may be seen, the available peroxide is dramatically reduced over a matter of days (not weeks) in the formulation containing precipitated silica.

Measurements were taken after the initial making of the formulation and then again after the formulation was stored in a non-reactive vessel for 13 days at 40° C. Compatibility was calculated as the peroxide percent measured after 13 days at 40° C. divided by the initial peroxide percent measured, then multiplied by 100. (Product placed at 40° C. for 13 days represents an extended shelf life, as it is generally accepted that one month stored at 40° C. roughly approximates storage at seven months at room temperature).

TABLE 6

| Weeks at | Percentage of Peroxide Remaining | | | | |
|---|---|---|---|---|---|
| 40° C. | 3A | 3B | 3C | 3D | 3E |
| 0 | 100 | 100 | 100 | 100 | 100 |
| 4 | 97 | 100 | 98 | 100 | 94 |
| 8 | 95 | 99 | 95 | 96 | 88 |
| 12 | 94 | 98 | 93 | 97 | 86 |

TABLE 5

| Ingredient | 3A Wt. % | 3B Wt. % | 3C Wt. % | 3D Wt. % | 3E Wt. % |
|---|---|---|---|---|---|
| LANETTE W | 15.000 | 15.000 | 15.000 | 15.000 | 15.000 |
| Sodium lauryl sulfate Powder | 1.875 | 1.875 | 1.875 | 1.875 | 1.875 |
| Water | 58.125 | 58.125 | 58.125 | 58.125 | 58.125 |
| (Total of above - forms 75% Gel Network Base) | (75.000) | (75.000) | (75.000) | (75.000) | (75.000) |
| Sodium Fluoride | 0.243 | 0.243 | 0.243 | 0.243 | 0.243 |
| Sucralose | 0.200 | 0.200 | 0.200 | 0.200 | 0.200 |
| Flavor | 1.000 | 1.000 | 1.000 | 1.000 | 1.000 |
| Sodium Acid Pyrophosphate | 0.300 | 0.300 | 0.300 | 0.300 | 0.300 |
| Disodium phosphate | 0.300 | 0.200 | 0.200 | 0.200 | 0.300 |
| TOSPEARL 145 | | 13.000 | | | |
| TOSPEARL 3120 | | | 13.000 | | |
| TOSPEARL CF 600 | | | | 13.000 | |
| TOSPEARL 150 | | | | | 13.000 |
| Hydrogen peroxide (35% soln) | 8.570 | 8.570 | 8.570 | 8.570 | 8.570 |
| Phosphoric Acid (estimated) | 0.330 | 0.420 | 0.230 | 0.320 | 0.380 |
| Water q.s. | 14.057 | 1.067 | 1.257 | 1.167 | 1.007 |
| Total => | 100.000 | 100.000 | 100.000 | 100.000 | 100.000 |
| pH Target => | 4.5 | 4.5 | 4.5 | 4.5 | 4.5 |

LANETTE W is a mixture of cetyl and stearyl alcohol (50:50) with sodium lauryl sulfate (approx. ratio of 90:10) commercially available from Cognis/BASF, located in Germany.
TOSPEARL materials commercially available from Momentive, New Jersey, USA.

Determining Peroxide Stability

The following methodology was used to determine the stability of the peroxide in a given formulation:

1) First, a 0.2 g sample of the formulation was gathered;
2) Then, 0.2000 g(+/−0.0200 g) of the peroxide gel was weighed into a 250 mL plastic beaker;
3) A stir bar and 100 mL of 0.04N H2SO4 was added to the beaker, the beaker covered with parafilmed and the contents stirred for at least ten minutes;
4) After stirring, 25 mL 10% KI solution and 3 drops of NH4-Molybdate were added to the beaker and the contents stirred for another 3-20 minutes;
5) The resulting mixture was analyzed via autotitration with 0.1N Na-Thiosulfate;

TABLE 7

| | 3F |
|---|---|
| LANETTE W | 15.000% |
| Sodium lauryl sulfate Powder | 1.875% |
| Water | 58.125% |
| Sodium fluoride | 0.243% |
| Sucralose | 0.200% |
| Flavor | 1.000% |
| SODIUM ACID PYROPHOSPHATE | 0.300% |
| Disodium phosphate | 0.200% |
| Precipitated Silica | 10.000% |
| Hydrogen peroxide (35% soln) | 8.570% |

TABLE 7-continued

|  | 3F |
|---|---|
| Phosphoric Acid (estimated) | 0.430% |
| Water q.s. | 79.057% |
| Total => | 100.000% |
| pH Target => | 4.5 |

LANETTE W is a mixture of cetyl and stearyl alcohol (50:50) with sodium lauryl sulfate (approx. ratio of 90:10) commercially available from Cognis/BASF, located in Germany.
ZEODENT 109 precipitated silica commercially available from the J. M. Huber Corporation.

TABLE 8

| Days at 40° C. | 3F Peroxide Remaining (%) |
|---|---|
| 0 | 100 |
| 7 | 63.3 |
| 14 | 53.3 |
| 21 | 35.3 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it will be obvious to those skilled in the art that various changes and modifications may be made without departing from the spirit and scope of the invention. It is therefore intended to cover in the appended claims all such changes and modifications that are within the scope of the invention.

We claim:

1. A method for cleaning and polishing teeth by brushing teeth with a dentifrice composition comprising from about 0.1% to about 40%, by weight of the composition, of an abrasive wherein the abrasive comprises polyorganosilsesquioxane particles.

2. The method of claim 1 wherein the composition further comprises a fluoride ion source selected from the group consisting of stannous fluoride, sodium fluoride, potassium fluoride, amine fluoride, sodium monofluorophosphate, zinc fluoride, and mixtures thereof.

3. The method of claim 2 wherein the composition comprises stannous fluoride.

4. The method of claim 2 wherein the composition comprises sodium fluoride.

5. The method of claim 1 wherein the polyorganosilsesquioxane particles have an average volume weighted mean particle size of from about 1 to about 20 microns.

6. The method of claim 5 wherein the polyorganosilsesquioxane particles have an average volume weighted mean particle size of from about 3 to about 7 microns.

7. The method of claim 5 wherein the composition further comprises an oxidizing agent.

8. The method of claim 1 wherein the composition further comprises a flavoring agent.

9. The method of claim 1 wherein the composition has a PCR from about 40 to about 200.

10. The method of claim 1 wherein the composition has a PCR of at least about 80.

11. The method of claim 1 wherein the composition has an RDA score of less than 200.

12. The method of claim 1 wherein the composition has an RDA score of less than 100.

13. The method of claim 1 wherein the polyorganosilsesquioxane particles are smooth surface particles.

14. A dentifrice composition comprising:
   a. from about 0.1% to about 40% of an abrasive wherein the abrasive comprises polyorganosilsesquioxane particles;
   b. from about 0.0025% to about 5.0% of a fluoride ion source selected from the group consisting of stannous fluoride, sodium fluoride, potassium fluoride, amine fluoride, sodium monofluorophosphate, zinc fluoride, and mixtures thereof;
   c. from about 0.001% to about 5% a flavoring agent.

15. The composition of claim 14 wherein the composition comprises stannous fluoride.

16. The composition of claim 14 wherein the composition comprises sodium fluoride.

17. The composition of claim 14 wherein the polyorganosilsesquioxane particles have an average volume weighted mean particle size of from about 1 to about 20 microns.

18. The composition of claim 15 wherein the polyorganosilsesquioxane particles have an average volume weighted mean particle size of from about 3 to about 7 microns.

19. The composition of claim 14 wherein the composition has a PCR of at least about 80.

20. The composition of claim 14 wherein the polyorganosilsesquioxane particles are smooth surface particles.

* * * * *